United States Patent
Peng et al.

(10) Patent No.: US 8,268,186 B2
(45) Date of Patent: *Sep. 18, 2012

(54) FLUORINATED AMPHOTERIC SURFACTANTS

(75) Inventors: Sheng Peng, Hockessin, DE (US);
Romain Severac, Moisson (FR);
Charles Kenneth Taylor, Thorofare, NJ (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 76 days.

This patent is subject to a terminal disclaimer.

(21) Appl. No.: 12/579,496

(22) Filed: Oct. 15, 2009

(65) Prior Publication Data

US 2011/0089362 A1    Apr. 21, 2011

(51) Int. Cl.
A62D 1/00 (2006.01)
C07C 311/03 (2006.01)
C07C 311/09 (2006.01)
C07C 311/24 (2006.01)

(52) U.S. Cl. .................................. 252/3; 252/2; 564/96
(58) Field of Classification Search .................. 252/2, 3; 564/96

See application file for complete search history.

(56) References Cited

U.S. PATENT DOCUMENTS

| | | | |
|---|---|---|---|
| 2,915,554 A | 12/1959 | Ahlbrecht et al. |
| 3,721,706 A | 3/1973 | Hoffmann et al. |
| 3,979,469 A | 9/1976 | Jager |
| 4,166,065 A | 8/1979 | Beck |
| 4,424,133 A | 1/1984 | Mulligan |
| 5,399,756 A | 3/1995 | Schneider et al. |
| 5,481,028 A | 1/1996 | Petrov et al. |
| 6,201,122 B1 | 3/2001 | Dams |
| 7,160,850 B2 | 1/2007 | Dams et al. |
| 2006/0149012 A1 | 7/2006 | Terrazas et al. |

FOREIGN PATENT DOCUMENTS

| | | |
|---|---|---|
| DE | 2829616 | 2/1979 |
| GB | 1304135 | 1/1973 |
| JP | 09286999 | 11/1997 |
| WO | 2005121290 | 12/2005 |
| WO | 2007020211 | 2/2007 |
| WO | WO 2007016359 A2 * | 2/2007 |
| WO | 2008045999 | 4/2008 |
| WO | 2008089391 | 7/2008 |

OTHER PUBLICATIONS

Banks et al. ("Organofluorine Chemistry", Plenum Press, New York, NY, 1994, p .335).*
Varadaraj et al.. Journal of Colloid and Interface Science, vol. 147, No. 2, pp. 387-395, Dec. 1991.*
Rosen, Journal of the Americal Oil Chemists' Society, vol. 49, pp. 293-297, May 1972.*
Balague et al., Synthesis of fluorinated telomers. Part 1. Telemerization of vinylidene fluoride with perfluoroalkyl iodides, Journal of Fluorine Chemistry, 70 (1955), 215-223, Elsevier Science S.A.
U.S. Appl. No. 12/579,488, filed Oct. 15, 2009, Peng.

* cited by examiner

*Primary Examiner* — Peter F Godenschwager

(57) ABSTRACT

A compound of Formula (I):

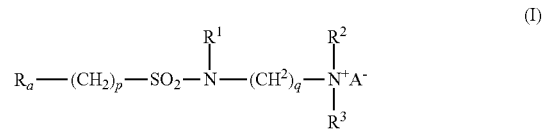

wherein
$R_a$ is linear or branched $F(CF_2)_n(CH_2CF_2)_m$—, or linear or branched $F(CF_2)_o$ interrupted by 1 to 6 catenary oxygen atoms, each oxygen bonded to two carbon atoms,
m is 1 to 4, n is 2 to 6, o is 2 to 7,
A is O or $(CH_2)_k$—COO,
$R^1$ is hydrogen or a methyl,
$R^2$ and $R^3$ are each independently alkyl having 1 to 6 carbon atoms, and
p, q and k are each independently integers from 1 to 10,
which is suitable for use as a surfactant and in fire fighting formulations.

19 Claims, No Drawings

FLUORINATED AMPHOTERIC SURFACTANTS

FIELD OF THE INVENTION

This invention relates to an amphoteric fluorinated sulfonate compounds which contain at least one vinylidene fluoride or oxygen moiety. The fluorinated sulfonate is useful as an amphoteric surfactant, and is particularly suitable for fire fighting applications.

BACKGROUND OF THE INVENTION

Fluorinated sulfonates are useful as surfactants in various applications. Commercially available fluorinated surfactants usually contain a perfluoroalkyl terminal chain. Honda, et al., in "Molecular Aggregation Structure and Surface Properties of Poly(fluoroalkylacrylate) Thin Films" Macromolecules (2005), 38(13), 5699-5705, disclose that a perfluoroalkyl chain of at least 8 carbons is necessary to maintain the perfluoroalkyl chains in a parallel orientation. For such perfluoroalkyl chains containing less than 8 continuous perfluorinated carbons, a reorientation occurs which decreases or eliminates the ability for exhibiting desirable surface properties. Thus longer perfluoroalkyl chains which contain a higher fluorine content at a given concentration typically provide better performance. However, the fluorinated materials derived from longer perfluoroalkyl chains are more expensive. Reducing the fluorine content with delivery of the same or better performance is therefore desirable.

U.S. Pat. No. 6,201,122, discloses a fluoroaliphatic radical-containing sulfonamido anionic compound, wherein the fluoroaliphatic radical group contains 3 to 20 carbons, and is preferably $C_nF_{2n+1}$ wherein n is 4 to 10. The compounds are useful as anionic surfactants in liquid systems. However, anionic surfactants are known to precipitate out of formulations commonly used in fire fighting applications and oilfield applications.

It is desirable to have surfactants containing partially fluorinated or shorter fully fluorinated terminal groups, or containing perfluoroalkyl chains interrupted with other atoms or moieties, to achieve equivalent or improved surface performance at lower expense. It is also desirable to have surfactants that do not precipitate out of end use formulations. The present invention provides such surfactants.

SUMMARY OF THE INVENTION

The present invention comprises a compound of formula (I):

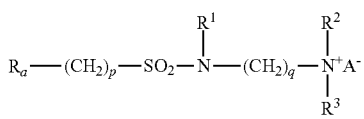

wherein
$R_a$ is linear or branched $F(CF_2)_n(CH_2CF_2)_m$—, or linear or branched $F(CF_2)_o$ interrupted by 1 to 6 catenary oxygen atoms, each oxygen bonded to two carbon atoms,
m is 1 to 4, n is 2 to 6, o is 2 to 7,
A is O or $(CH_2)_k$—COO,
$R^1$ is hydrogen or a methyl,
$R^2$ and $R^3$ are each independently alkyl having 1 to 6 carbon atoms, and
p, q and k are each independently integers from 1 to 10.

The present invention further comprises a fire fighting agent, a foaming agent, and a fire fighting foam concentrate, each comprising a compound of formula (I) as defined above.

The present invention further comprises a method of extinguishing a fire comprising contacting the fire with a composition comprising a compound of formula (I) as defined above.

DETAILED DESCRIPTION

Trademarks are shown herein in upper case.

The present invention comprises a compound that reduces surface tension of aqueous medium and is useful as a surfactant and in fire fighting compositions. The compounds are effective to lower the surface tension of aqueous medium at low concentrations and have amphiphilic properties.

The present invention comprises a compound of formula (I):

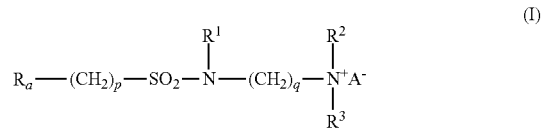

wherein
$R_a$ is linear or branched $F(CF_2)_n(CH_2CF_2)_m$—, or linear or branched $F(CF_2)_o$ interrupted by 1 to 6 catenary oxygen atoms, each oxygen bonded to two carbon atoms,
m is 1 to 4, n is 2 to 6, o is 2 to 7,
A is O or $(CH_2)_k$—COO,
$R^1$ is hydrogen or a methyl,
$R^2$ and $R^3$ are each independently alkyl having 1 to 6 carbon atoms, and
p, q and k are each independently integers from 1 to 10.

Preferred compounds of formula (I) are those wherein $R_a$ is $F(CF_2)_n(CH_2CF_2)_m$— wherein n is 2 to 6, and m is 1 to 2, and more preferred wherein n is 6. Also preferred are those compounds of formula (I) wherein $R_a$ is $F(CF_2)_sO(CF_2)_t$— wherein s and t are each independently 1 to 6, provided that (s+t) is 2 to 7, and more preferred wherein (s+t) is 5 to 7.

The compounds of formula (I) are prepared from an intermediate amine of the formula (II):

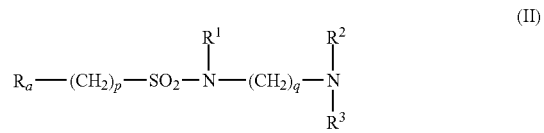

wherein $R_a$, p, q, $R^1$, $R^2$, and $R^3$ are the same as defined above in formula (I). Compounds of formula (II) are reacted with alpha-ethylenic acids, aliphatic lactones or beta-halo-carboxylic acids to produce the compounds of formula (Ia). For example, the intermediate amine in formula (II) is reacted with sodium chloroacetate at temperature of about 78° C. for about 24 hours to produce compounds of formula (I) wherein A is $(CH_2)_k$—C(O)O. Alternatively, the intermediate amine in formula (II) is oxidized to produce the compounds of Formula (I) wherein A is O. For example, the intermediate amine of formula (II) is reacted with hydrogen peroxide at a temperature of about 50° C. for about 56 hours, followed by a second addition of hydrogen peroxide, and the reaction is maintained at about 50° C. for an extra 12 hours to produce compounds of formula (I) wherein A is O.

The intermediate amine of formula (II) is synthesized by reacting an amine, preferably diaminopropylamine, with a fluorinated sulfonyl chloride of formula (III)

wherein Ra and p are as defined in formula (I). For example, the intermediate sulfonyl chloride of formula (III) is reacted with diaminopropylamine at a temperature of about 70° C. for about 8 to 12 hours (overnight) to produce an amine of formula (II).

The fluorinated sulfonyl chloride of formula (III) is formed by reacting a fluorinated thiocyanate of formula (IV)

wherein Ra and p are as defined in formula (I), with chlorine and acetic acid at about 45° C. to 50° C. For example, the intermediate thiocyanate of formula (IV) is reacted with chlorine in acetic acid over 10 hours at about 45 to 50° C. in an autoclave. The product is heated with stirring at about 70° C. and hot water (70° C.) added. The organic layer is separated to obtain the product formula (III).

The fluorinated thiocyanate of formula (IV) is prepared by reacting ethylene iodides of formula (V)

with potassium thiocyanate in the presence of trioctylmethylammonium chloride at 90° C. in water. After phase separation, the product is purified by distillation under vacuum.

The ethylene iodides of formula (V) are prepared by reacting fluorinated iodides of formula (VI).

wherein $R_a$ is as defined above in formula (I), with ethylene by the procedures described in U.S. Pat. No. 3,979,469, (Ciba-Geigy, 1976). For example, 115 g of $R_a$—I is autoclaved together with 0.5 g of CuCl, 1.5 g of $Al_2O_3$, and 1 g of ethanolamine. After cooling to −70° C., evacuating, and sparging with nitrogen, 20 g of ethylene is passed in under pressure. The autoclave is then kept for 6 hours at 150° C. and 25 kp/cm2, and then degassed to yield the product.

Fluorinated iodides of formula (VI) having the formula $F(CF_2)_n(CH_2CF_2)_mI$ are produced by the known telomerization of vinylidene fluoride (VDF) with linear or branched perfluoroalkyl iodides. For example, see Balague, et al, "Synthesis of fluorinated telomers, Part 1, Telomerization of vinylidene fluoride with perfluoroalkyl iodides", J. Fluorine Chem. (1995), 70(2), 215-23. For example the reaction can be carried out thermally in an autoclave after flushing with nitrogen gas at a temperature of 175° C. to 230° C. using an equimolar ratio of telegen/VDF for about 15 hours. Preferred examples of iodides needed to make compounds of formula (I) wherein $R_a$ is $F(CF_2)_n(CH_2CF_2)_m$— include $F(CF_2)_6(CH_2CF_2)I$ and $F(CF_2)_6(CH_2CF_2)_2I$.

Fluorinated iodides of formula (VI) having the formula $F(CF_2)_sO(CF_2)_tI$ wherein s and t are each independently 1 to 4, and (s+t) is 2 to 7, can be prepared from perfluoroalkyl ether iodides which can be made by the procedure described in U.S. Pat. No. 5,481,028. Preferred is the process in Example 8 wherein perfluoro-n-propyl vinyl ether (0.3M) is reacted with $BF_3$ (0.15M) for 18 hours at 50° C. in a shaker tube, generating the product, which is then subjected to isolation and distillation procedures. Preferred examples of iodides needed to make compounds of formula (I) wherein $R_a$ is $F(CF_2)_sO(CF_2)_t$— are $F(CF_2)_3O(CF_2)_2I$, $F(CF_2)_2O(CF_2)_4I$, $F(CF_2)_4O(CF_2)_2I$, and $F(CF_2)_3O(CF_2)_4I$.

In one preferred embodiment of this invention, the surfactant is a compound of (I) having the following formula:

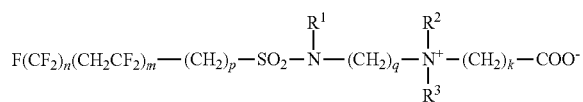

wherein m, n, p, k, $R^1$, $R^2$, and $R^3$ are as defined above in formula (I).

In a further preferred embodiment of this invention, the surfactant is a compound of (I) having the following formula:

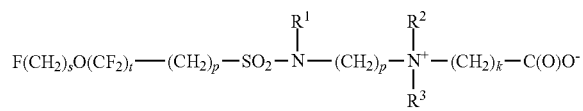

wherein s, t, p, q, k, $R^1$, $R^2$, and $R^3$ are as defined above in formula (I).

In a further preferred embodiment of this invention, the surfactant is a compound of (I) having the following formula:

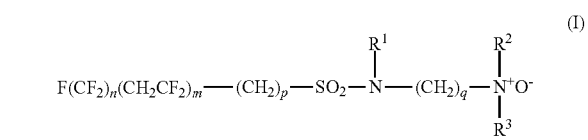

wherein m, n, p, k, $R^1$, $R^2$, and $R^3$ are as defined above in formula (I).

In a further preferred embodiment of this invention, the surfactant is a compound of (I) having the following formula:

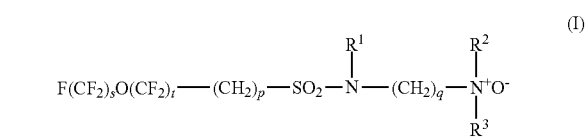

wherein s, t, p, q, $R^1$, $R^2$, and $R^3$ are as defined above in formula (I).

The compounds of formula (I) have excellent surface active properties and significantly reduce the surface tension of aqueous solutions at low concentrations. Uses include, but are not limited to, filming, foaming, wetting, leveling, dispersing and as emulsifying agents. Preferrably, the compounds of this invention are useful active ingredients in fire fighting agents.

The compounds of formula (I) are useful as surfactants and are capable of lowering surface tensions when added to aqueous media at low concentrations. These compounds are capable of lowering the surface tension of aqueous media to values less than about 25 milli-newtons per meter, preferably less than about 20 milli-newtons per meter, at a concentration of the surfactant in the medium of less than about 0.5% by weight, preferably less than about 0.2% by weight, and more preferably less than 0.1% by weight. These surfactants are characterized by its efficiency in lowering the surface tension at low concentrations by selective adsorption on the interface, which is determined by the amphiphilic nature of the surfactants.

The present invention further comprises a fire fighting agent comprising a compound of formula (I) of this invention as described above. The fire fighting agent typically further comprises water or a solvent. Preferred solvents are alcohols or glycols, for example ethanol or 1,2-propylene glycol. The fire fighting agent can also further comprise a hydrocarbon surfactant. Suitable hydrocarbon surfactants are available commercially. Examples include SIMULSOL SL8 available from Seppic, Paris La Defense, France; SULFETAL 4069 available from Zschimmer & Schwartz, Lahnstein, Germany; TRITON X100 available from Roche, Basil, Switzerland; and AMPHOTENSID GB2009 available from Zschimmer & Schwartz, Lahnstein, Germany.

The fire fighting agent is in the form of a liquid or foam. Fire fighting foam concentrates are compositions useful in extinguishing combustible liquid fires, particularly those caused by hydrocarbons and/or polar liquids. Fire fighting foams generate a water film over the fuel surface separating the flammable source from the flames, thus extinguishing the fire. After the fire is extinguished, the foams also suppress the flammable vapors from releasing, reducing the risk of burn-back, or re-ignition, of the flammable vapors. Typically at the time of use, the foam concentrates are diluted with water, usually municipal water or seawater, generally at a concentration about 6% by weight of the agent in the water. Other suitable concentrations used for extinguishing fires include solution of 1% and 3% by weight. Generally, the agent is agitated with water and a fire fighting foamed solution is formed prior to application. One mode of agitation is to pass the fire fighting agent and water solution through a fire hose nozzle where mechanical agitation takes place with incorporation of air, which generates an extinguishing foam used to combat combustible liquid fires. The foaming solution may contain other additives that assist in extinguishing fires such as FORAFAC 1268, commercially available from E. I du Pont de Nemours and Company, Wilmington, Del.

The present invention further comprises a method of extinguishing a fire comprising contacting the fire with a composition containing a compound of formula (I) as described above. The compound of formula (I) is typically applied to the fire as a dilution in water, one or more solvents, or mixtures thereof, at a concentration of from about 1% to about 6% by weight of formula (I). The compound can be applied as a liquid or a foam. The compound can also be mixed with one or more surfactants as discussed above prior to contacting with the fire. The compound of formula (I) is contacted with the fire by using a conventional mechanical fire extinguisher, conventional hose with nozzle, or other known means. Typically the compound is applied continuously until the fire is extinguished.

The present invention provides several advantages. The compound of formula (I) is amphoteric and has excellent surfactant properties. It is stable in typical fire fighting formulations without precipitating out of solution, as demonstrated by Examples 1 to 10 herein. The compound of formula (I) is useful as a fire fighting agent in the form of a liquid or foam. It is useful to extinguish fires quickly and aids in suppressing re-ignition of the fire. The compound of formula (I) contains a short terminal perfluoroalkyl chain of six or less fluorinated carbons, and thus is less expensive than prior art compounds containing longer perfluoroalkyl chains, while providing the same or better surfactant and fire fighting properties.

Test Methods and Materials

The following test methods and materials (intermediates) were used in the Examples herein. Proton and $^{19}$F NMR as well as electrospray mass spectroscopy were used to confirm compositions of the intermediates and Examples.

Test Methods

Test Method 1—Surface Tension Measurement

The surface tension of the examples was measured via a Kruess Tensiometer, K11 Version 2.501, in accordance with instructions with the equipment. The Wilhelmy Plate method was used. A vertical plate of known perimeter was attached to a balance, and the force due to wetting was measured. Ten replicates were tested of each dilution, and the following machine settings were used: Plate Method SFT, 1.0 sec interval, 40.2 mm wetted length, 10 reading limit, 2 dynbes/cm min Standard Deviation, and 9.80665 m/s$^2$ Gr. Acc. Lower surface tension indicated superior performance.

A stock solution was prepared for the highest concentration of fluorosurfactant example to be analyzed. The concentration of the solutions was by percent active ingredient, weight percent, or fluorine content. This stock solution was prepared in deionized water. The stock solution was stirred overnight (for approximately 12 hours) to ensure complete mixing. Additional concentrations of the fluorosurfactant example for analysis were made by diluting the stock solution according to the equation $M_iV_i=M_fV_f$, where $M_i$ is the concentration of the stock solution, $M_f$ is the concentration of the final solution, $V_f$ is the final volume of the sample, and $V_i$ is the volume of the stock solution that is needed in order to formulate the final sample. The concentration dilution samples were shaken thoroughly and then left to sit undisturbed for 30 minutes. These samples were then mixed and poured into a small container. The surface tension was measured using a Kruess Tensiometer, K11 Version 2.501 in accordance with instructions with the equipment as described above. Lower surface tension indicated superior performance.

Test Method 2—Petri-Dish Spreading in Cyclohexane

Cyclohexane (70 mL) was added to a Petri-dish (black-painted). The examples (100 µL) of the following invention were used to prepare two formulations. Formulation 1 was made of 0.1098 g fluorinated surfactant of Formula (I), 0.2927 g SULFETAL 4069 hydrocarbon surfactant (Zschimmer & Schwarz, Lahnstein, Germany) based on 100% active ingredient and DOWANOL (Dow Chemical, Midland, Mich.) in 50 mL tap water. Formulation 2 was made of 0.1154 g fluorinated surfactant of Formula (I), 0.3077 g of AMPHOTENSID GB2009 hydrocarbon surfactant (Zschimmer & Schwarz, Lahnstein, Germany) based on 100% active ingredient and 0.5385 g DOWANOL (Dow Chemical, Midland Mich.) in 50 mL tap water. Each formulation was added to the centre of the dish as a solution using a micro-pipette, swirling clockwise and working outwards. The time was recorded from the deposition of the first drop of solution until complete coverage was observed. The stop watch was stopped after one minute and the coverage percentage noted if complete coverage was not achieved. The higher the coverage percentage, the better the performance; At the same coverage percentage, the shorter the time, the better the performance.

Test Method 3—Fire Extinguishing and Re-Ignition Time Tests

Extinguishing times were measured according to the following procedure. A flammable solvent, heptane or isopropanol, (150 mL) was poured into a circular metal container with an internal diameter of 115 mm. An aqueous solution was prepared by diluting a composition to be tested to 6 percent by weight in tap water. This aqueous solution was the foaming solution used for fire extinguishing. A rotary stirrer, composed of a motor and a metal rod with paddles, was used to stir the aqueous solutions to produced foam at adjustable speeds of 0 to 2,800 rpm. The paddles were placed at the bottom of a cylindrical container equipped with an inlet orifice located at the bottom and with an outlet orifice located at the top. A metering pump transferred, via the inlet orifice, the aqueous solution to the bottom of the cylindrical container; foam was produced on contact with the rotating paddles. The foam was discharged as it was formed, via the outlet orifice. The throughput of the pump and the rotational speed of the rod were adjusted so that foam was continuously produced with a stationary foam throughput equal to about 40 g per minute. When the foam throughput was stabilized, the flammable solvent was ignited. After the flammable solvent burned for 90 seconds, the foam was poured into the metal container via a single point situated on the circumference. When the flammable solvent was completely extinguished, the extinguishing time was recorded. The aqueous solutions with the best performance were those for which the extinguishing time was as low as possible.

Re-ignition time tests were measured according to the following procedure. The composition to be tested was diluted to 6% by weight with tap water, but also included in some instances a fluorinated surfactant, FORAFAC 1268, commercially available from E. I. du Pont de Nemours, and Company, Wilmington, Del. The test was only performed on compositions that produced extinguishing times that were less than 120 seconds. For re-ignition time tests, the foam was poured over the solvent after the fire was extinguished in the initial fire extinguishing time test. The foam was poured for 120 s. Sixty seconds after the pouring of the foam was complete, the contents of a re-ignition vessel, a metal container with a diameter of 55 mm and height of 40 mm and was filled with flammable solvent, heptane or isopropanol, to a height of 20 mm, was ignited. The re-ignition vessel was then placed at the center of the metal container described in the fire extinguishing test, with the surface of solvent present in the said container being kept covered with foam. When 25% of the foam that initially covered the surface was destroyed, the re-ignition time was recorded. The greater the re-ignition time, the better the ability of the foam to prevent the resurgence of the fire.

Materials

Intermediate 1

$C_3F_7OCF_2CF_2I$ (100 g, 0.24 mol) and benzoyl peroxide (3 g) were charged to a pressure vessel under nitrogen. A series of three vacuum/nitrogen gas sequences was then executed at −50° C. and ethylene (18 g, 0.64 mol) was introduced. The vessel was heated for 24 hour at 110° C. The autoclave was cooled to 0° C. and opened after degassing. Then the product was collected in a bottle. The product was distilled resulting in 80 g of $C_3F_7OCF_2CF_2CH_2CH_2I$ in 80% yield. The boiling point was 5660° C. at 25 mm Hg (3333 Pa).

Potassium thiocynate (21.34 g, 0.22 mol) was added to a mixture of $C_3F_7OCF_2CF_2CH_2CH_2I$ (50 g, 0.11 mol) and trioctylmethylammonium chloride (0.2222 g) in 50 g of water. The reaction was heated overnight at 90° C. After phase separation, the product $C_3F_7OCF_2CF_2CH_2CH_2SCN$ was distilled as a colorless liquid (32 g, 78%).

Chlorine gas (132 g, 1.86 mol) and water (47 g, 2.6 mol) were fed into a mixture of $C_3F_7OCF_2CF_2CH_2CH_2SCN$ (231 g, 0.62 mol) and acetic acid (130 g, 2.17 mol) over 10 hours at 4550° C. in an autoclave. A further 10 g of chlorine was added over 3 hours at 45° C. and heated at this temperature for 1 hour. The product was heated in a flask with a stir bar at 70° C. and 149 mL of hot water (70° C.) was added. The organic layer was separated, followed by adding of toluene (125 g). The product in toluene was washed with 3.5% solution of brine (149 mL) at 70° C. twice. After the second wash, a Dean-Stark strap was set up to strip off water. The final product was 70% of $C_3F_7OCF_2CF_2CH_2CH_2SO_2Cl$ (228 g, 90%) by weight in toluene.

$C_3F_7OCF_2CF_2CH_2CH_2SO_2Cl$ (100 g, 0.242 mol, 66.8% in toluene) was added dropwise to a mixture of dimethylaminopropylamine (DMAPA) at 45° C. After the addition, the reaction was heated at 75° C. overnight. The reaction mass was filtered and the wet cake was washed with 60° C. toluene. After stripping off the toluene, the concentrated organic product was washed with 200 mL of 95° C. deionized water. The product Intermediate 1, $C_3F_7OCF_2CF_2CH_2CH_2SO_2N(H)$—$CH_2CH_2CH_2N(CH_3)_2$ (101 g, 87.2%) was obtained as an amber colored solids after removing water under reduced pressure.

Intermediate 2

Ethylene (25 g, 0.53 mol) was introduced to an autoclave charged with $C_4F_9CH_2CF_2I$ (217 g, 0.87 mol) and d-(+)-limonene (1 g), and then the reactor was heated at 240° C. for 12 hours. The product, $C_4F_9CH_2CF_2CH_2CH_2I$, was obtained via vacuum distillation 81~91° C. at 19~24 mmHg in 62% yield. Potassium thiocynate (21.34 g, 0.22 mol) was added to a mixture of $C_4F_9CH_2CF_2CH_2CH_2I$ (50 g, 0.11 mol) and trioctylmethylammonium chloride (0.2222 g) in 50 g of water. The reaction was heated overnight at 90° C. After phase separation, the product $C_4F_9CH_2CF_2CH_2CH_2SCN$ was distilled as a colorless liquid (38 g, 95%).

Chlorine gas (118 g, 1.66 mol) and water (40 g, 2.22 mol) were fed into a mixture of $C_4F_9CH_2CF_2CH_2CH_2SCN$ (205 g, 0.56 mol) and acetic acid (109 g, 1.82 mol) over 10 hours at 4550° C. in an autoclave. The product was heated in a flask with a stir bar at 70° C. and hot water (70° C.) was added. The organic layer was separated, followed by adding of toluene (216.25 g). The product in toluene was washed with 3.5% solution of brine at 70° C. twice. After the second wash, a Dean-Stark strap was set up to strip off water. The final product was 70% of $C_4F_9CH_2CF_2CH_2CH_2SO_2Cl$ (228 g, 39%) by weight in toluene.

$C_4F_9CH_2CF_2CH_2CH_2SO_2Cl$ (100 g, 0.23 mol, 70.3% in toluene) was added dropwise to a mixture of dimethylaminopropylamine (DMAPA) at 45° C. After the addition, the reaction was heated at 75° C. overnight. The reaction mass was filtered and the wet cake was washed with 60° C. toluene. After stripping off the toluene, the concentrated organic product was washed with 200 mL of 95° C. deionized water. The product Intermediate 2, $C_4F_9CH_2CF_2CH_2CH_2SO_2N(H)$—$CH_2CH_2CH_2N(CH_3)_2$ (106 g, 96.8%) was obtained as a brown colored solids after removing water under reduced pressure.

Intermediate 3

$C_4F_9(CH_2CF_2)_2I$ (327 g, 0.69 mol) was charged to a Hastalloy C shaker tube reactor followed by a series of three vacuum/$N_2$ gas sequences. Ethylene (35 g, 2.57 mol) was introduced and the vessel heated to 240° C. for 3 hours, maintaining a pressure of 250 psig. Vacuum distillation of 2 combined runs provided 572 g (83%) of product, $C_4F_9(CH_2CF_2)_2CH_2CH_2I$, with boiling point 111~120° C. at 16~20 mmHg.

The flask was charged with $C_4F_9(CH_2CF_2)_2CH_2CH_2I$ (500 g, 0.996 mol), potassium thiocyanate (194 g, 1.99 mol) and trioctylmethylammoniumchloride (ALIQUAT 336) (4.02 g, 0.00995 mol) under nitrogen. Deionized water (500 g, 27.8 mol) was added and the reaction mixture was heated to 90° C. for 18 hours. The organic layer was separated in a glass separating funnel and washed with hot (70° C.) deionized water. The product was distilled on a high vacuum system resulting in 407 g (94.3%) of $C_4F_9(CH_2CF_2)_2CH_2CH_2SCN$; by 129~133° C./1.0 mmHg.

An autoclave was charged with $C_4F_9(CH_2CF_2)_2CH_2CH_2SCN$ (269 g, 0.62 mol) and acetic acid (130 g, 2.17 mol) under nitrogen and heated to 45~50° C. Chlorine gas (132 g, 1.86 mol) was fed at an estimated rate for 10 hours and deionized water (47 g, 2.60 mol) was fed at an estimated rate for 8 hours. After feeding, the reaction was left to stir at 45~50° C. for 1 hour. A second addition of chlorine gas (25 g, 0.352 mol) was fed over 2.5 hours at 45~50° C. and left to stir for 1 hour. The crude product was heated at 70° C. and washed with deionized water (149 g, 8.28 mol). The organic layer was separated in a glass separating funnel and added to toluene (125 g, 1.36 mol), then washed twice with a 3.5% solution of sodium chloride (149 g). A Dean Stark trap was used to strip off excess solvent and the product was set to 70.2% active ingredient in toluene resulting in 359 g (85.6%) of $C_4F_9(CH_2CF_2)_2CH_2CH_2SO_2Cl$.

Dimethylaminopropylamine (41 g, 0.401 mol) and toluene (62.6 g, 0.679 mol) were charged to a 3-neck round-bottom flask equipped with a reflux condenser, nitrogen inlet, addition funnel, magnetic stirrer and temperature probe. The mixture was heated to 45° C. followed by the drop wise addition of $C_4F_9(CH_2CF_2)_2CH_2CH_2SO_2Cl$ (100 g, 0.211 mol) resulting in an exotherm. The reaction mixture was heated to 75° C. for 24 hours, filtered through a fritted glass filter with a slight vacuum and the wet cake washed with warm (60° C.) toluene (89.5 g, 0.971 mol). The solvent was evaporated under reduced pressure and the organic product was washed with warm (95° C.) deionized water (200 g, 11.1 mol), separated in a glass separating funnel and re-washed with a 4% solution of sodium chloride (200 g). Any remaining solvent was evaporated under reduced pressure to give 100 g (87.7%) of Intermediate 3, $C_4F_9(CH_2CF_2)_2CH_2CH_2SO_2N(H)$—$CH_2CH_2CH_2N(CH_3)_2$; mp 52~58° C.

Intermediate 4

$C_6F_{13}CH_2CF_2I$ (760 g, 1.49 mol) was charged to a Hastalloy C rocker bomb reactor. A series of three vacuum/$N_2$ gas sequences were then executed and an initial charge of ethylene (5 g, 0.179 mol) was introduced. The vessel was heated to 240° C. and ethylene (72 g, 2.57 mol) was introduced to maintain the autogenous pressure. The reaction mixture was held at 240° C. for 12 hours. This gave 789.1 g (98.5%) product, $C_6F_{13}CH_2CF_2CH_2CH_2I$ with mp 65-68° C.

The flask was charged with $C_6F_{13}CH_2CF_2CH_2CH_2I$ (500 g, 0.929 mol), potassium thiocyanate (180.6 g, 1.86 mol) and trioctylmethylammoniumchloride (ALIQUAT 336) (3.75 g, 0.00929 mol) under nitrogen. Deionized water (500 g, 27.8 mol) was added and the reaction mixture was heated to 90° C. for 18 hours. The organic layer was separated in a glass separating funnel and washed with hot (70° C.) deionized water. The product was distilled on a high vacuum system resulting in 386 g (88.6%) of $C_6F_{13}CH_2CF_2CH_2CH_2SCN$; by 104~106° C./0.75~0.50 mmHg, mp 35~39° C.

An autoclave was charged with a mixture of $C_6F_{13}CH_2CF_2CH_2CH_2SCN$ (291 g, 0.62 mol) and acetic acid (130 g, 2.17 mol) under nitrogen and heated to 45~50° C. Chlorine gas (132 g, 1.86 mol) was fed at an estimated rate for 10 hours and deionized water (47 g, 2.60 mol) was fed at an estimated rate for 8 hours. After feeding, the reaction was left to stir at 45~50° C. for 1 hour. A second addition of chlorine gas (25 g, 0.352 mol) was fed over 110 minutes at 45~50° C. and left to stir for 1 hour. The crude product was heated at 70° C. and washed with deionized water (149 g, 8.28 mol). The organic layer was separated in a glass separating funnel and added to toluene (125 g, 1.36 mol), then washed twice with a 3.5% solution of sodium chloride (149 g). A Dean Stark trap was used to strip off excess solvent and the product was set to 68.0% active ingredient in toluene resulting in 421 g (90.4%) of $C_6F_{13}CH_2CF_2CH_2CH_2SO_2Cl$.

Dimethylaminopropylamine (76.1 g, 0.754 mol) and toluene (116.3 g, 1.262 mol) were charged to a 3-neck round-bottom flask equipped with a reflux condenser, nitrogen inlet, addition funnel, magnetic stirrer and temperature probe. The mixture was heated to 35° C. followed by the drop wise addition of $C_6F_{13}CH_2CF_2CH_2CH_2SO_2Cl$ (200 g, 0.392 mol) resulting in an exotherm. The reaction mixture was heated to 75° C. for 24 hours, filtered through a fritted glass filter with a slight vacuum and the wet cake washed with warm (60° C.) toluene (166.1 g, 1.803 mol). The solvent was evaporated under reduced pressure and the organic product was washed with warm (95° C.) deionized water (400 g, 22.2 mol), separated in a glass separating funnel and re-washed with a 4% solution of sodium chloride (400 g). Any remaining solvent was evaporated under reduced pressure to give 217 g (96.2%) of Intermediate 4, $C_6F_{13}CH_2CF_2CH_2CH_2SON(H)$—$CH_2CH_2CH_2N(CH_3)_2$; mp 82~85° C.

Intermediate 5

$C_6F_{13}(CH_2CF_2)_2I$ (580 g, 1.01 mol) was charged to a Hastalloy C rocker bomb reactor. A series of three vacuum/$N_2$ gas sequences were then executed and an initial charge of ethylene (5 g, 0.179 mol) was introduced. The vessel was heated to 240° C. and ethylene (46 g, 1.64 mol) was introduced to maintain the autogeneous pressure. The reaction mixture was held at 240° C. for 12 hours. This resulted in 591.7 g (97.3%) of $C_6F_{13}(CH_2CF_2)_2CH_2CH_2I$ with mp 68~72° C.

The flask was charged with $C_6F_{13}(CH_2CF_2)_2CH_2CH_2I$ (500 g, 0.831 mol), potassium thiocyanate (161.3 g, 1.66 mol) and trioctylmethylammoniumchloride (ALIQUAT 336) (3.36 g, 0.00831 mol) under nitrogen. Deionized water (500 g, 27.8 mol) was added and the reaction mixture was heated to 90° C. for 18 hours. The organic layer was separated in a glass separating funnel and washed with hot (70° C.) deionized water. The product was distilled on a high vacuum system resulting in 381.6 g (86.1%) of $C_6F_{13}(CH_2CF_2)_2CH_2CH_2SCN$; by 115~130° C./0.75~0.30 mmHg, mp 43~47° C.

An autoclave was charged with a mixture of $C_6F_{13}(CH_2CF_2)_2CH_2CH_2$—SCN (331 g, 0.62 mol) and acetic acid (130 g, 2.17 mol) under nitrogen and heated to 45~50° C. Chlorine gas (132 g, 1.86 mol) was fed at an estimated rate for 10 hours and deionized water (47 g, 2.60 mol) was fed at an estimated rate for 8 hours. After feeding, the reaction was left to stir at 45~50° C. for 1 hour. A second addition of chlorine gas (25 g, 0.352 mol) was fed over 110 minutes at 45~50° C. and left to stir for 1 hour. The crude product was heated at 70° C. and washed with deionized water (149 g, 8.28 mol). The organic layer was separated in a glass separating funnel and added to toluene (125 g, 1.36 mol), then washed twice with a 3.5% solution of sodium chloride (149 g). A Dean Stark trap was used to strip off excess solvent and the product was set to 75.5% active ingredient in toluene resulting in 419 g (88.9%) of $C_6F_{13}(CH_2CF_2)_2CH_2CH_2SO_2Cl$.

Dimethylaminopropylamine (67.6 g, 0.661 mol) and toluene (103.3 g, 1.121 mol) were charged to a 3-neck round-bottom flask equipped with a reflux condenser, nitrogen inlet, addition funnel, magnetic stirrer and temperature probe. The mixture was heated to 35° C. followed by the drop wise addition of $C_6F_{13}(CH_2CF_2)_2CH_2CH_2SO_2Cl$ (200 g, 0.348 mol) resulting in an exotherm. The reaction mixture was heated to 75° C. for 24 hours, filtered through a fritted glass filter with a slight vacuum and the wet cake washed with warm (60° C.) toluene (147.5 g, 1.601 mol). The solvent was evaporated under reduced pressure and the organic product was washed with warm (95° C.) deionized water (400 g, 22.2 mol), separated in a glass separating funnel and re-washed with a 4% solution of sodium chloride (400 g). Any remaining solvent was evaporated under reduced pressure to give 212 g (95.2%) of Intermediate 5, $C_6F_{13}(CH_2CF_2)_2CH_2CH_2SO_2N$ (H)—$CH_2CH_2CH_2N(CH_3)_2$; mp 72~76° C.

EXAMPLES

Example 1

Intermediate 1, $C_3F_7OCF_2CF_2CH_2CH_2SO_2N(H)$—$CH_2CH_2CH_2N(CH_3)_2$ (7 g, 0.0146 mol), was added to a mixture of ethanol (5.4 g), deionized water (0.193 g, 0.0107 mol), sodium chloroacetate (1.74 g, 0.0149 mol) and celite (2.75 g). The reaction was refluxed overnight and filtered. The filtrate, $C_3F_7OCF_2CF_2CH_2CH_2SO_2$—$N(H)CH_2CH_2CH_2N$ $(CH_3)_2$+$CH_2C(O)O^-$, was diluted to a 27% active ingredient with ethanol and water. The product was tested using Test Methods 1 and 2. Results are listed in Tables 1 and 2.

Example 2

A mixture of Intermediate 1, $C_3F_7OCF_2CF_2CH_2CH_2SO_2N$ (H)—$CH_2CH_2CH_2N(CH_3)_2$ (20 g, 0.0418 mol), and ethanol (16.7 g, 0.320 mol) was charged to a 3-neck round bottom flask equipped with a reflux condenser, nitrogen inlet, addition funnel, magnetic stirrer and temperature probe and heated to 50° C. Hydrogen peroxide (1.75 g, 0.514 mol) was added drop wise and maintained at 50° C. for 56 hours. A second addition of hydrogen peroxide (1.75 g, 0.514 mol) was added to the reaction and maintained at 50° C. for an extra 12 hours Manganese (IV) oxide (0.004 g, 0.0000460 mol) was added gradually and held at 50° C. for an additional 16 hours. The reaction mixture was then filtered through a fritted glass filter with a slight vacuum and excess solvent was evaporated. This yielded 11.8 g (51.0%) of $C_3F_7OCF_2CF_2CH_2CH_2SO_2N(H)$—$CH_2CH_2CH_2N^+$ $(CH_3)_2O^-$ that was diluted with ethanol (8.9 g, 0.193 mol) and deionized water (8.9 g, 0.494 mol) to give a 40% active ingredient concentrated solution. The product was tested using Test Methods 1 and 2. Results are listed in Tables 1 and 2.

Example 3

Intermediate 2, $C_4F_9CH_2CF_2CH_2CH_2SO_2N(H)$—$CH_2CH_2CH_2N(CH_3)_2$ (7 g, 0.0147 mol), was added to a mixture of ethanol (5.4 g), deionized water (0.193 g, 0.0107 mol), sodium chloroacetate (1.74 g, 0.0149 mol) and celite (2.75 g). The reaction was refluxed overnight and filtered. The filtrate, $C_4F_9CH_2CF_2CH_2CH_2SO_2N(H)$—$CH_2CH_2CH_2N$ $(CH_3)_2$+$CH_2C(O)O^{31}$, was diluted to a 27% active ingredient with ethanol and water. The product was tested using Test Methods 1 and 2. Results are listed in Tables 1 and 2.

Example 4

A 3-neck round-bottom flask equipped with a reflux condenser, nitrogen inlet, addition funnel, magnetic stirrer and temperature probe was charged with Intermediate 3, $C_4F_9$ $(CH_2CF_2)_2CH_2CH_2SO_2N(H)$—$CH_2CH_2CH_2N(CH_3)_2$ (20 g, 0.0370 mol), ethanol (13.6 g, 0.296 mol), deionized water (0.5 g, 0.0270 mol) and sodium chloroacetate (4.4 g, 0.0377 mol). The reaction mixture was heated to 78° C. for 24 hours, filtered through a fitted glass filter with a slight vacuum and the wet cake washed with warm (75° C.) ethanol (150 g, 3.26 mol). The solvent was then evaporated under reduced pressure to give 9 g (40.7%) of product $C_4F_9(CH_2CF_2)_2$ $CH_2CH_2SO_2N(H)CH_2CH_2CH_2N(CH_3)_2$+$CH_2C(O)O^-$. The final product was diluted with ethanol (11.7 g, 0.254 mol) and deionized water (12.7 g, 0.704 mol) to give a 27% active ingredient concentrated solution. The product was tested using Test Methods 1 and 2. Results are listed in Tables 1 and 2.

Example 5

A 3-neck round-bottom flask equipped with a reflux condenser, nitrogen inlet, addition funnel, magnetic stirrer and temperature probe was charged with Intermediate 4, $C_6F_{13}CH_2CF_2CH_2CH_2SON(H)$—$CH_2CH_2CH_2N(CH_3)_2$ (50 g, 0.0868 mol), ethanol (31.9 g, 0.694 mol), deionized water (1.1 g, 0.0634 mol) and sodium chloroacetate (10.3 g, 0.0885 mol). The reaction mixture was heated to 78° C. for 24 hours, filtered through a fitted glass filter with a slight vacuum and the wet cake washed with warm (75° C.) ethanol (150 g, 3.26 mol). The solvent was evaporated to give 56 g (99.0%) of $C_6F_{13}CH_2CF_2CH_2CH_2SON(H)$—$CH_2CH_2CH_2N(CH_3)_2$+ $CH_2C(O)O^-$. The product was tested using Test Methods 1, 2, and 3. Results are listed in Tables 1, 2, and 3.

Example 6

A 3-neck round-bottom flask equipped with a reflux condenser, nitrogen inlet, addition funnel, magnetic stirrer and temperature probe was charged with Intermediate 5, $C_6F_{13}$ $(CH_2CF_2)_2CH_2CH_2SO_2N(H)$—$CH_2CH_2CH_2N(CH_3)_2$ (60 g, 0.0937 mol), ethanol (34.5 g, 0.750 mol), deionized water (1.2 g, 0.0684 mol) and sodium chloroacetate (11.1 g, 0.0956 mol). The reaction mixture was heated to 78° C. for 24 hours, filtered through a fritted glass filter with a slight vacuum and the wet cake washed with warm (75° C.) ethanol (150 g, 3.26 mol). The solvent was evaporated to give 62 g (94.8%) of $C_6F_{13}(CH_2CF_2)_2CH_2CH_2SO_2N(H)$—$CH_2CH_2CH_2$ $N(CH_3)_2$+$CH_2C(O)O^-$. The product was tested using Test Methods 1, 2, and 3. Results are listed in Tables 1, 2, and 3.

Example 7

A mixture of Intermediate 2, $C_4F_9CH_2CF_2CH_2CH_2SO_2N$ (H)—$CH_2CH_2CH_2N(CH_3)_2$ (20 g, 0.0420 mol), and ethanol (16.7 g, 0.363 mol) was charged to a 3-neck round bottom flask equipped with a reflux condenser, nitrogen inlet, addition funnel, magnetic stirrer and temperature probe and heated to 50° C. Hydrogen peroxide (4.4 g, 0.129 mol) was added drop wise and maintained at 50° C. for 17 hours. Manganese (IV) oxide (0.0102 g, 0.000118 mol) was added gradually and held at 50° C. for an additional 16 hours. The reaction mixture was then filtered through a fritted glass filter with a slight vacuum and excess solvent was evaporated under reduced pressure. This yielded 14.3 g (69.0%) of $C_4F_9CH_2CF_2CH_2CH_2SO_2N(H)$—$CH_2CH_2CH_2N$ $(CH_3)_2O^{31}$, which was then diluted with ethanol (10.7 g, 0.233 mol) and deionized water (10.7 g, 0.594 mol) to give a 40% active ingredient concentrated solution. The product was tested using Test Methods 1 and 2. Results are listed in Tables 1 and 2.

Example 8

A mixture of Intermediate 3, $C_4F_9(CH_2CF_2)_2$ $CH_2CH_2SO_2N(H)$—$CH_2CH_2CH_2N(CH_3)_2$ (20 g, 0.0370 mol), and ethanol (14.7 g, 0.320 mol) was charged to a 3-neck round bottom flask equipped with a reflux condenser, nitrogen inlet, addition funnel, magnetic stirrer and temperature probe and heated to 50° C. Hydrogen peroxide (3.9 g, 0.114 mol) was added drop wise and maintained at 50° C. for 24 hours. Manganese (IV) oxide (0.009 g, 0.000104 mol) was added gradually and held at 50° C. for an additional 16 hours. The reaction mixture was then filtered through a fitted glass filter with a slight vacuum and excess solvent was evaporated. This yielded 15.2 g (74.1%) of $C_4F_9(CH_2CF_2)_2$ $CH_2CH_2SO_2N(H)$—$CH_2CH_2CH_2N^+(CH_3)_2O^-$ that was diluted with ethanol (11.4 g, 0.248 mol) and deionized water (11.4 g, 0.633 mol) to give a 40% active ingredient concentrated solution. The product was tested using Test Methods 1 and 2. Results are listed in Tables 1 and 2.

Example 9

A mixture of Intermediate 4, $C_6F_{13}CH_2CF_2CH_2CH_2SON(H)$—$CH_2CH_2CH_2N(CH_3)_2$ (50 g, 0.0868 mol), and ethanol (34.5 g, 0.751 mol) was charged to a 3-neck round bottom flask equipped with a reflux condenser, nitrogen inlet, addition funnel, magnetic stirrer and temperature probe and heated to 50° C. Hydrogen peroxide (9.1 g, 0.267 mol) was added drop wise and maintained at 50° C. for 24 hours. Manganese (IV) oxide (0.0211 g, 0.000243 mol) was added gradually and held at 50° C. for an additional 3 hours. The reaction mixture was then filtered through a fritted glass filter with a slight vacuum and excess solvent was evaporated. This yielded 31.7 g (61.6%) of $C_6F_{13}CH_2CF_2CH_2CH_2SON(H)$—$CH_2CH_2CH_2N^+(CH_3)_2O^-$. The product was tested using Test Methods 1 and 2. Results are listed in Tables 1 and 2.

Example 10

A mixture of Intermediate 5, $C_6F_{13}(CH_2CF_2)_2$ $CH_2CH_2SO_2N(H)$—$CH_2CH_2CH_2N(CH_3)_2$ (60 g, 0.0937 mol), and ethanol (37.3 g, 0.811 mol) was charged to a 3-neck round bottom flask equipped with a reflux condenser, nitrogen inlet, addition funnel, magnetic stirrer and temperature probe and heated to 50° C. Hydrogen peroxide (9.8 g, 0.289 mol) was added drop wise and maintained at 50° C. for 24 hours. Manganese (IV) oxide (0.023 g, 0.000262 mol) was added gradually and held at 50° C. for an additional 3 hours. The reaction mixture was then filtered through a fitted glass filter with a slight vacuum and excess solvent was evaporated. This yielded 58 g (94.3%) of $C_6F_{13}(CH_2CF_2)_2CH_2CH_2SO_2N(H)$—$CH_2CH_2CH_2N^+(CH_3)_2O^-$. The product was tested using Test Methods 1 and 2. Results are listed in Tables 1 and 2.

Comparative Example A

The procedure of the Intermediate 1 was repeated, but a perfluoroalkylethyl iodide of the formula $F(CF_2)_nCH_2CH_2I$ was used, wherein n ranged from 6 to 8 as the fluorinated iodide. The typical mixture was as follows: 0.68% of n=4, 67.8% of n=6, 19.5% of n=8, 7.2% of n=10, 2.4% of n=12, 0.79% of n=14, 0.23% of n=16, 0.07% of n=18 and 0.02% of n=20. The resulting product, $F(CF_2)_nCH_2CH_2SO_2N(H)$—$CH_2CH_2CH_2N(CH_3)_2$ was tested according to Test Methods 1, 2 and 3. Results are in Tables 1, 2 and 3.

Comparative Example B

The procedure for Intermediate 1 was repeated but a perfluoroalkylethyl iodide of the formula $F(CF_2)_6CH_2CH_2I$ was used. The resulting product intermediate was then reacted using the procedure of Example 1. The resulting product, $F(CF_2)_6CH_2CH_2SO_2N(H)$—$CH_2CH_2CH_2N(CH_3)_2$+$CH_2C(O)O^-$, was according to Test Method 3. Results are in Table 3.

TABLE 1

| Surface Tension in Deionized Water (dynes/cm) at 23° C. | | | | | | | |
|---|---|---|---|---|---|---|---|
| Example | 1% | 0.5% | 0.2% | 0.1% | 0.05% | 0.01% | 0.005% |
| Example 1 | 18.2 | 15.2 | 15.6 | 17.3 | 17.9 | 20.7 | 20.3 |
| Example 2 | 15.8 | 15.7 | 17.1 | 16.1 | 16.5 | 20.0 | 21.4 |
| Example 3 | 17.7 | 18.9 | 15.9 | 18.4 | 22.6 | 25.3 | 24.4 |
| Example 4 | 18.3 | 17.9 | 16.9 | 19.2 | 16.7 | 20.6 | 27.5 |
| Example 5 | 16.7 | 16.5 | 16.8 | 17.3 | 17.9 | 17.6 | 17.8 |
| Example 6 | 18.9 | 18.9 | 18.2 | 18.5 | 17.7 | 19.5 | 20.0 |
| Example 7 | 16.1 | 18.4 | 16.9 | 17.6 | 21.2 | 19.4 | 25.1 |
| Example 8 | 16.8 | 17.8 | 16.6 | 17.9 | 17.2 | 19.4 | 19.7 |
| Example 9 | 17.3 | 17.5 | 16.9 | 21.8 | 18.8 | 19.0 | 18.9 |
| Example 10 | 16.8 | 16.1 | 16.3 | 17.6 | 17.9 | 19.3 | 21.3 |
| Comparative Example A | 17.3 | 17.3 | 17.5 | 18.0 | 18.5 | 18.1 | 20.9 |

Normal surface tension of deionized water is 72 dyne/cm. When the above surfactants were added at a specified rate, the surface tension of each aqueous solution was reduced significantly. All the Examples 1 to 10 of the invention containing less than 8 fully fluorinated carbons showed comparable or better performance to Comparative Example A containing a mixture of perfluoralkyls of 4 to 20 carbons.

TABLE 2

| Spreading Test in Cyclohexane | | |
|---|---|---|
| Examples | Formulation 1 | Formulation 2 |
| Example 1 | 100% in 3 s | 100% in 3 s |
| Example 2 | 90% in 3 s | 100% in 15 s |
| Example 3 | 100% in 2 s | 100% in 2 s |
| Example 4 | 100% in 2 s | 100% in 2 s |
| Example 5 | 100% in 40 s | 100% in 4 s |
| Example 6 | 50% in 25 s | 100% in 9 s |
| Example 7 | 100% in 2 s | 100% in 4 s |
| Example 8 | 100% in 5 s | 100% in 0 s |
| Example 9 | 100% in 19 s | 70% in 45 s |
| Example 10 | 50% in 15 s | 100% in 9 s |
| Comparative Example A | 30% in 30 s | 100% in 3 s |

In this test a spread of 100% in less than one minute is desired for fire fighting applications. From the data in Table 2 it can be seen that Examples 1 to 8 and 10 of the present invention showed equal to or better performance than the Comparative Example A, despite containing less fluorine than Comparative Example A.

TABLE 3

| Fire Extinguishing and Re-ignition Times | | | | |
|---|---|---|---|---|
| Example* | Additive | Flammable Solvent | Fire Extinguishing Time (in mintues:seconds) | Re-ignition Time (in minutes:seconds) |
| 5 | — | Heptane | 1:10 | 14:50 |
| 6 | — | Heptane | 1:14 | 17:10 |

TABLE 3-continued

Fire Extinguishing and Re-ignition Times

| Example* | Additive | Flammable Solvent | Fire Extinguishing Time (in mintues:seconds) | Re-ignition Time (in minutes:seconds) |
|---|---|---|---|---|
| Comparative Example A | — | Heptane | 1:19 | 17:00 |
| Comparative Example B | — | Heptane | 1:20 | 13:30 |
| 5 | FORAFAC 1268 | Isopropanol | 0:58 | 7:30 |
| Comparative Example A | — | Isopropanol | 1:02 | 7:20 |
| Comparative Example B | FORAFAC 1268 | Isopropanol | 1:13 | 6:15 |

*Examples were diluted to 6% by weight with tap water prior to use
— indicates that no additive was used Overall, compositions of Examples 5 and 6 of the present invention provided faster (superior) performance on the fire extinguishing tests than the Comparative Examples A and B with heptane as a flammable solvent. Re-ignition times of both Examples 5 and 6 were slower (superior) to Comparable Example B, and Example 6 was slower than Comparable Example A. With isopropanol as a flammable solvent, and with an additive (FORAFAC 1268) Example 5 was faster (superior) to both Comparative Examples A and B in the fire extinguishing tests. Example 5 was also slower (superior) than Comparable Examples A and B in the re-ignition test with the isopropanol solvent.

Examples 5 and 6 each contained 6 carbons in the terminal perfluoroalkyl chain, and contained a total of 7 and 8 fully fluorinated carbons, respectfully, while Comparative Example A contained a mixture of perfluroalkyls containing 4 to 20 carbons. Thus Comparative Example A contained far more fluorine than Examples 5 and 6, yet Examples 5 and 6 demonstrated comparable or superior performance. Comparative Example B contained 6 carbons in a continuous terminal perfluoroalkyl chain, while Examples 5 and 6 contained an interrupting $CH_2CF_2$ moiety. The data demonstrates that compounds containing such an interrupted perfluoroalkyl can perform equally to or better than one with a continuous perfluoroalkyl.

What is claimed is:

1. A compound of Formula (I):

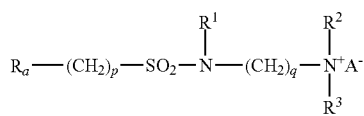

wherein
$R_a$ is linear $F(CF_2)_n(CH_2CF_2)_m—$,
m is 1 to 4, n is 2 to 6,
A is O or $(CH_2)_k—COO$,
$R^1$ is hydrogen or a methyl,
$R^2$ and $R^3$ are each independently alkyl having 1 to 6 carbon atoms, and
p, q and k are each independently integers from 1 to 10, said compound capable of lowering surface tension when added to aqueous media and useful in fire-fighting agents.

2. The compound of claim 1 wherein $R_a$ is $F(CF_2)_n(CH_2CF_2)_m—$ wherein n is 2 to 6 and m is 1 to 2.

3. The compound of claim 1 having a surface tension of about 25 mN/m or less at a concentration of about 0.1% by weight in water.

4. The compound of claim 1 having a surface tension of about 20 mN/m or less at a concentration of about 0.5% by weight in water.

5. The compound of claim 1 in the form of a foam.

6. The compound of claim 1 in the form of a fire fighting agent.

7. The agent of claim 6 further comprising water or solvent.

8. The agent of claim 6 further comprising one or more surfactants.

9. The agent of claim 6 in the form of a foam.

10. A method of extinguishing a fire comprising contacting the fire with a composition containing a compound of claim 1.

11. A compound of Formula (I):

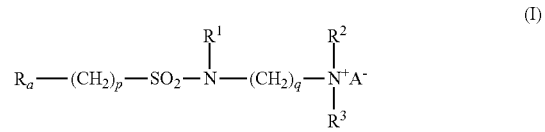

wherein
$R_a$ is linear $F(CF_2)_o$ interrupted by 1 to 6 catenary oxygen atoms, each oxygen bonded to two carbon atoms,
o is 2 to 7,
A is O or $(CH_2)_k—COO$,
$R^1$ is hydrogen or a methyl,
$R^2$ and $R^3$ are each independently alkyl having 1 to 6 carbon atoms, and
p, q and k are each independently integers from 1 to 10, said compound capable of lowering surface tension when added to aqueous media.

12. The compound of claim 11 wherein $R_a$ is $F(CF_2)_sO(CF_2)_t—$ wherein s and t are each 1 to 6 provided that (s+t) is 2 to 7.

13. The compound of claim 11 having a surface tension of about 25 mN/m or less at a concentration of about 0.1% by weight in water.

14. The compound of claim 11 in the form of a foam.

15. The compound of claim 11 in the form of a fire fighting agent.

16. The agent of claim 15 further comprising water or solvent.

17. The agent of claim 16 further comprising one or more surfactants.

18. The agent of claim 16 in the form of a foam.

19. A method of extinguishing a fire comprising contacting the fire with a composition containing a compound of claim 11.

* * * * *